(12) United States Patent
Vaillant et al.

(10) Patent No.: US 6,510,241 B1
(45) Date of Patent: Jan. 21, 2003

(54) PROCESS FOR RECONSTRUCTING A THREE-DIMENSIONAL IMAGE OF AN OBJECT

(75) Inventors: Regis Vaillant, Villebon sur Yvette (FR); Laurant Launay, Versailles (FR); Rene Romeas, Palaiseau (FR); Yves Lucien Marie Trousset, Palaiseau (FR)

(73) Assignee: GE Medical Systems SA, Buc (FR)

( * ) Notice: Subject to any disclaimer, the term of this patent is extended or adjusted under 35 U.S.C. 154(b) by 0 days.

(21) Appl. No.: 09/326,013

(22) Filed: Jun. 4, 1999

(30) Foreign Application Priority Data

Jun. 11, 1998 (FR) .................................. 98 07371

(51) Int. Cl.[7] ................................................ G06K 9/00
(52) U.S. Cl. .................. 382/154; 382/130; 382/274; 382/285; 700/98; 700/120; 345/419
(58) Field of Search .......................... 382/154, 285, 382/274, 130, 133; 378/4; 700/98, 120, 182; 345/419, 420

(56) References Cited

U.S. PATENT DOCUMENTS

| | | | | |
|---|---|---|---|---|
| 5,241,471 A | * | 8/1993 | Trousset et al. | 382/274 |
| 5,381,518 A | * | 1/1995 | Drebin et al. | 345/424 |
| 5,588,033 A | * | 12/1996 | Yeung | 378/4 |
| 5,963,612 A | * | 10/1999 | Navab | 378/4 |
| 6,320,928 B1 | * | 11/2001 | Vaillant et al. | 378/4 |

FOREIGN PATENT DOCUMENTS

| | | |
|---|---|---|
| FR | 8903606 | 9/1990 |
| FR | 8916906 | 6/1991 |
| FR | 9300804 | 7/1994 |
| FR | 2752975 | 3/1998 |
| WO | 9742592 | 11/1997 |

OTHER PUBLICATIONS

Delaney et al, "Multiresolution Tomographic Reconstruction Using Wavelets," IEEE Trans on Image Proc. Jun. 1995, No. 6, p. 799–813.

Rabadi et al, "Iterative Multiresolution Algorithm for Image Reconstruction From the Magnitude of Its Fourier Transform" Optical Engineering, vol. 35, No. 4, Apr. 1966, p. 1015–1023.

(List continued on next page.)

*Primary Examiner*—Bhavesh Mehta
*Assistant Examiner*—Gregory Desire
(74) *Attorney, Agent, or Firm*—Jay L. Chaskin

(57) ABSTRACT

The process comprises a calibration of the apparatus, in which a virtual volume surrounding the object is generated and broken down into voxels, an acquisition of the set of numbered projected two-dimensional images, and a reconstruction of the three-dimensional image from the projected acquired two-dimensional images, and from an iterative algebraic image reconstruction algorithm. A first iteration of the algorithm is performed with a predetermined initial image resolution so as to obtain, at the end of this first iteration, first density values for the voxels of the volume, at least one part of the voxels of the virtual volume is subdivided into several sets, respectively, corresponding to different image resolutions that are multiples or sub-multiples of the initial resolution, and during each subsequent iteration of the algorithm, the algorithm is successively aplied to each of the sets of voxels.

21 Claims, 3 Drawing Sheets

OTHER PUBLICATIONS

Gordon et al, "Algebraic Reconstruction Techniques (Art) for Three–Dimensional Electron Microscopy and X–Ray Photography", J. Theo. Biol. (1970) vol. 29, p 471–481.

Jain, "Fundamentals of Digital Image Processing", Prentice Hall, Sep. 1988, Engineering/Science/Mathematics.

Parker et al, "Three–Dimensional Reconstruction and Flow Measurements of Coronary Arteries Using Multi–View Digital Angiography", New Developments in Quantitative Coronary Angiography, Kluwer Academic Publishers, 1988 pp 225–247.

Garreau et al "A Knowledge–Based Approach for 3–D Reconstruction and Labeling of Vascular Networks From Biplane Angiographic Projections", IEEE Trans. on Medical Imaging, vol. 10, No. 2, Jun. 1991, p. 122–131.

Hawkes et al, "The Accurate 3–D Reconstruction of the Geometric Configuration of Vascular Trees From X–Ray Recordings", Physics and Engineering on Medical Imaging, 1987, p. 250–256.

\* cited by examiner

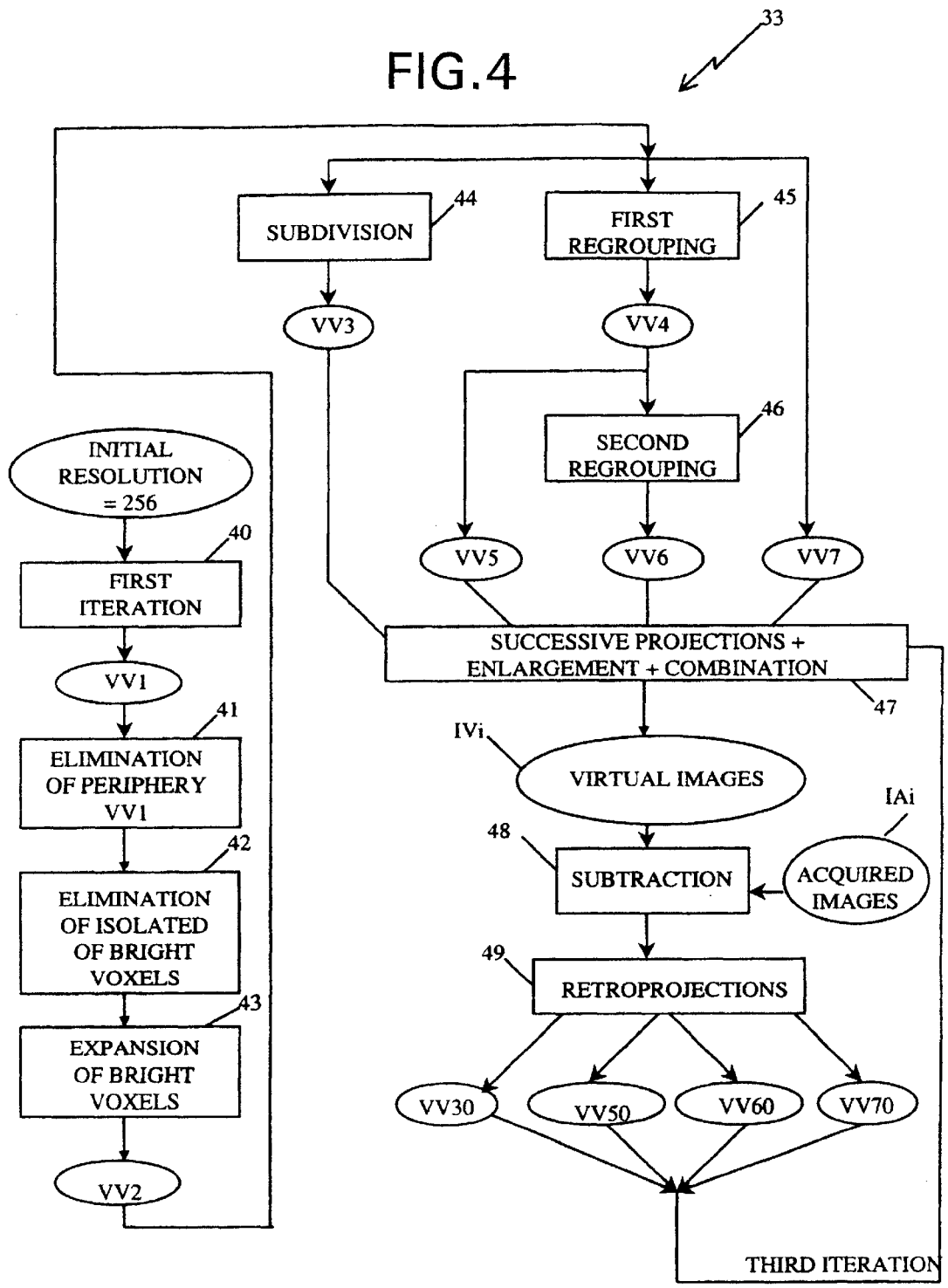

PROCESS FOR RECONSTRUCTING A THREE-DIMENSIONAL IMAGE OF AN OBJECT

BACKGROUND OF THE INVENTION

The invention relates to the reconstruction of a three-dimensional image of an object from a set of projected two-dimensional images of said object obtained from different positions of an imaging apparatus around the object.

It has a particularly advantageous application in the medical field that involves the reconstruction of the internal structures of a patient under examination, particularly the reconstruction of angiographic images, i.e., the obtainment of images of vascular trees opacified by the injection of a contrast medium.

The invention can nevertheless have applications in other fields, particularly in nondestructive industrial testing, in which tests of the same type as the medical tests are conducted.

In the medical field, the projected two-dimensional images of the object, for example a patient's head, are generally obtained by the rotation of an X-ray imaging apparatus that revolves around the object.

There are essentially two types of reconstruction algorithms in X-ray imaging.

A first type provides for a retroprojection and filtering calculation, or even a Fourrier transform reconstruction in several dimensions.

A second type, the one to the invention relates, involves iterative reconstruction methods, also referred to as algebraic. The principle of such an algebraic algorithm is well known to one skilled in the art and has already been the subject of many publications. We refer in particular to the article by GORDON, BENDER and HERMAN entitled, "Algebraic Reconstruction Technique for Three-dimensional Electron Microscopy and X-ray Photography," THEO. BIOL Journal 29, pages 471 to 781 (1970), or the book by Anil K. JAIN entitled "Fundamentals of Digital Image Processing," Prentice Hall Information and System Sciences Series, Thomas Kailath Series Edition, or French Patent Application No. 89 03606 or No. 89 16906.

Briefly, after a calibration of the apparatus used in order to determine, in particular, the parameters for the projection, into the projection planes of the acquired images, of an observed volume broken down into elementary volume elements or voxels (which calibration parameters form projection matrices), the algebraic image reconstruction algorithm is used to reconstruct the three-dimensional volume from these projected two-dimensional images. The basic principle of this algorithm is to initialize the voxels of the volume to a predetermined initial value, for example a null value, and to iterate the following operations a certain number of times: the projection of the voxels into the plane of each acquired image so as to obtain a virtual image, the determination of the difference between the projected volume (virtual image) and the corresponding acquired image, followed by the projection of this difference back into the volume. After a certain number of iterations, an estimated value representing the density of the contrast medium injected into the X-rayed vessels is obtained for each voxel, making it possible to display the three-dimensional cartography of these X-rayed vessels.

The acquired images generally have a resolution equal to 512, i.e., they comprise 512 rows and 512 columns of pixels. If the image reconstruction algorithm were applied to the acquired images in their entirety, it would result in the processing of about 128 million voxels, which is too high a number and in any case would not be very useful, since the vascular structures that generally need to be displayed typically occupy about 2% of the virtual volume.

Also, it has been proposed to reduce the resolution value of the acquired images, by calculating averages of four pixels, in order to arrive at a resolution value of 256, which results in a reduction of the virtual volume. After a first iteration of the algorithm performed on each image, a first rough representation of the location of the objects of interest is already obtained, making it possible to select, for the subsequent iterations, a subset of p voxels and to eliminate the others. Each of these remaining p voxels is then subdivided into eight, so that the projection of such a subdivided voxel corresponds to ½ a pixel of resolution 256, i.e., a pixel of resolution 512. The sub-sequent iterations of the algorithm, in practice two iterations, are then performed on all of these subdivided voxels.

Even after the elimination of a certain number of voxels, the set of subdivided voxels amounts to about 32 million, which is still a very high number, and which translates into a non-negligible cost in terms of calculation time. One solution could consist of eliminating more voxels in order to further reduce the number of subdivided voxels remaining. But if this route is taken, artifacts are produced in the images displayed, due to the underrepresentation of the volume of the data handled by the image reconstruction algorithm.

BRIEF SUMMARY OF THE INVENTION

An embodiment of the invention reduces the calculation time of the processor implementing the image reconstruction algorithm while not modifying the quality of the images obtained, i.e., by specifically not introducing artifacts into the images.

An embodiment of the invention is a process for reconstructing a three-dimensional image of an object from a set of numbered projected two-dimensional images of the object obtained from various positions of an imaging apparatus around the object. This process comprises a calibration of the apparatus in which a virtual volume surrounding the object is generated and broken down into voxels, an acquisition of the set of numbered projected two-dimensional images, and a reconstruction of the three-dimensional image from the projected acquired two-dimensional images, and from an iterative algebraic image reconstruction algorithm.

According to an embodiment of the invention, a first iteration of the algorithm is performed with a predetermined initial image resolution so as to obtain, at the end of this first iteration, first density values for the voxels of said volume. At least one part of the voxels of the virtual volume are subdivided into several sets, respectively corresponding to different image resolutions that are multiples or sub-multiples of the initial resolution. And during each subsequent iteration of the algorithm, the algorithm is successively applied to each of the sets of voxels.

In other words, an embodiment of the invention makes it possible to apply the iterative algebraic image reconstruction algorithm to a multi-resolution volume. In this volume, voxels which a priori represent the objects of interest to be displayed are selected, and they are divided in order to increase the resolution. The other voxels, which are of less interest since they do not directly relate to the objects to be displayed, are either left as is, or regrouped at least once in order to reduce the value of the resolution, but they are still used for the image reconstitution calculations, making it possible to ultimately obtain images of very good quality with a reduced calculation time.

According to one mode of implementation of the invention, during each subsequent iteration of the algorithm, i.e., during each iteration beginning with the second one, a virtual image is determined for each projected acquired image by successively combining the elementary virtual images respectively obtained from the projections of the corresponding sets of voxels into the acquisition plane of the projected acquired image.

More precisely, in an embodiment of the invention and particularly in order to further reduce the calculation time, the elementary virtual images are preferably generated in the increasing order of the resolution values, beginning with the elementary virtual image corresponding to the lowest resolution value (for example 64), and after an elementary virtual image is determined, a scaling is performed in order to obtain a so-called "enlarged" virtual image whose resolution corresponds to that of the next elementary virtual image to be determined, and said enlarged virtual image is combined with the next elementary virtual image.

Generally, according to one mode of implementation of the invention, projected two-dimensional having a predetermined base resolution (for example r=512) are acquired. An initial resolution is chosen which is equal to a sub-multiple of the base resolution (for example r/2=256), and chosen from among said different image resolutions are said base resolution (r), the initial resolution (r/2) and at least one first additional resolution (for example (r/4=128), which is a sub-multiple of the initial resolution (r/2).

According to one mode of implementation of the invention, a first density threshold is generated as a function of a predetermined selection criterion. Each voxel having a density higher than or equal to the first threshold is subdivided into a first number of subdivided voxels, the first number (typically 8) being defined based on the relationship between the base resolution and the initial resolution, all of which sub-divided voxels form a first set of voxels corresponding to said base resolution (r=512). At least some of the voxels whose density is lower than the first threshold, and which meet a predetermined regrouping criterion, are regrouped so as to form regrouped voxels which form a second set of voxels corresponding to the first additional resolution (r/4=128), the number (typically 8) of regrouped voxels in each group being based on the relationship between the initial resolution (r=256) and the first additional resolution (128). And, the voxels whose density is lower than the first threshold, and which do not meet the predetermined regrouping criterion, form a third set of voxels corresponding to the initial resolution (256).

By way of example, a voxel meets the regrouping criterion if each of the coordinates of the center of the voxel is a multiple of 2 and if the density of each voxel adjacent to said voxel is lower than the first threshold.

It is also possible, and preferable, to once again regroup the voxels which have already been regrouped and which meet the regrouping criterion, in order to form a fourth set of voxels corresponding to a second additional resolution (for example 64), which is a sub-multiple of the first additional resolution (for example 128).

Generally, the part of the voxels of the virtual volume that is subdivided can be obtained by eliminating the voxels located in a layer of predetermined thickness of the surface of the volume. It has actually been observed that the image reconstruction algorithm tends to create high densities on the periphery of the volume, which do not in fact correspond to objects of interest to be displayed.

It is also possible to eliminate from the virtual volume the isolated voxels whose density is higher than a second predetermined threshold. In fact, it has been observed that an isolated voxel of high density does not correspond to an object of interest.

Furthermore, after the first iteration of the algorithm, each voxel whose density value is higher than or equal to a third predetermined threshold is preferably assigned a density value equal to the maximum density value obtained among the density values of said voxel and the adjacent voxels. In other words, at this point an expansion of the high-density voxels is preferably performed, in order to further improve the quality of the display of the objects of interest.

BRIEF DESCRIPTION OF THE DRAWING

Other advantages and characteristics of the invention will emerge from the study of the detailed description of a non-limiting mode of implementation, and of the attached drawings, in which:

FIG. 4 illustrates in greater detail a part of the flow chart of FIG. 3.

DETAILED DESCRIPTION OF THE INVENTION

Although the invention is not limited to this, the application of the process to the reconstruction of a three-dimensional angiographic image of a patient, specifically his head, will now be described.

Figure 1:
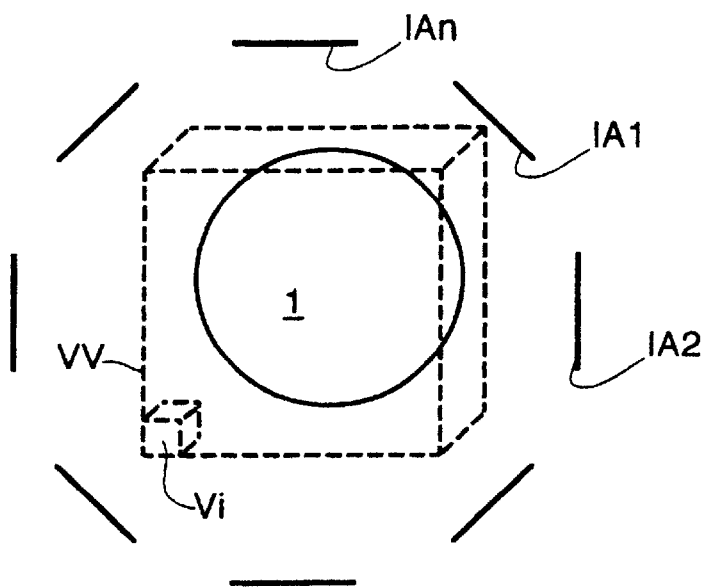
FIG. 1 schematically illustrates a set of projected two-dimensional images around an object.
Figure 2:
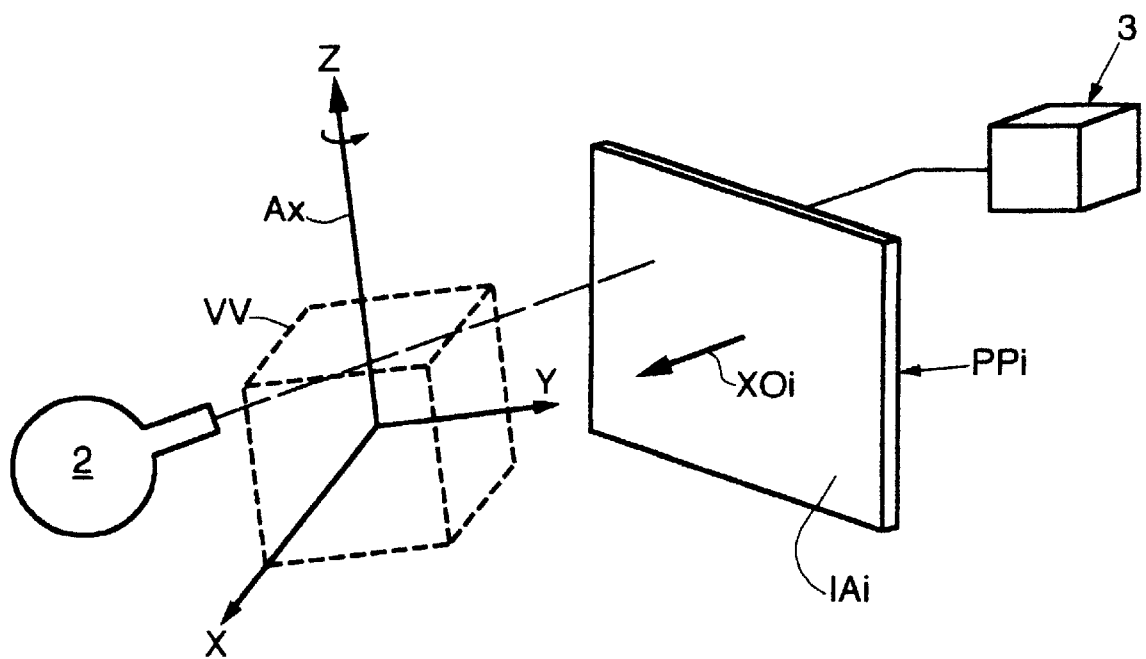
FIG. 2 illustrates in greater detail the acquisition of one of these projected two-dimensional images.

Referring more particularly to FIGS. 1 and 2, the imaging system that can be used to implement the invention makes it possible to obtain a set of acquired two-dimensional images IA1–IAn, in this case obtained by the rotation around the head 1 of a patient of an X-ray source 2. In fact, as is standard in angiography, each acquired image IAi is a subtracted image which is, for example, obtained by means of standard logarithmic subtraction technique from two X-rays taken at the same incidence, before and after the injection of a contrast medium into the vascular tree whose three-dimensional image is intended to be reconstructed.

Each acquired image IAi is obtained from a two-dimensional radiation detector, for example of the luminance amplifier type used in radiology, disposed opposite the X-ray tube in a plane called the projection plane PPi. The various projection planes are obtained from the various angular positions of the detector rotating around the patient's head. The normal XOi to the projection plane PPi defines the optical axis of the acquired image IAi. The detector is connected to processing means 3 specifically comprising sampling means connected to a microprocessor incorporating in software form in its associated program memory the algebraic image reconstruction algorithm used in the invention and in general, all of the functional means that allow the implementation of the process according to the invention.

In the case of an X-ray imaging system composed of an X-ray source and a two-dimensional detector, the geometric operation involved in the production of the acquired image is a conical projection of a scanned object, which occupies a three-dimensional space, into a two-dimensional space which is that of the projection plane corresponding to the detection plane. The geometric parameters that completely describe the various conical projections must be known. It is too imprecise, and often impossible, to access these parameters directly, i.e., for example by directly measuring the distance between the X-ray source and the detector in the acquisition system.

What is called the "calibration" of an imaging system is the operation that results in the precise indirect knowledge of the geometric parameters involved in the production of an image. The standard principle, which is known, is based on the use of a known geometric phantom in the three-dimensional space, a two-dimensional projection of which is acquired. More precisely, the calibration comprises the following steps:

using a known object, the calibration phantom, having a certain number of characteristic points whose position in space is known from coordinates measured relative to a reference point specific to this object;

acquiring the image of this phantom under the geometric conditions of a point of view (or incidence) intended to be calibrated;

recognizing the projections of the characteristic points into the image.

For this purpose, each characteristic point of the object is associated with its plotting in the projected acquired image;

inverting, in the mathematical sense, the equation system describing the projection;

and finally, obtaining all the parameters of the projection for the given point of view.

A frequently used shape for a geometric calibration phantom is that of a cube in whose eight corners are disposed metal balls that are opaque to X-rays. Calibration being an operation that is known to one skilled in the art, it will not be described in further detail, in that several publications have already described the principle of a manual geometric calibration. The following articles in particular may be cited:

(1) D. L. Parker, J. Wu, D. L. Pole, R. Van Bree, G. R. Caputp and H. W. Marshall, "Three-Dimensional Reconstruction and Flow Measurements of Coronary Arteries Using Multi-View Digital Angiography," in New Developments in Quantitative Coronary Arteriography, J. C. Reiber and P. W. Serruys, Eds., pp. 225–247, Kluwer Academic Publishers, 1988;

(2) D. J. Hawks, A. C. F. Colchester and C. R. Mol; "The Accurate 3-D Reconstruction of the Geometric Configuration of the Vascular Trees from X-Ray Recordings," in Physics and Engineering of Medical Imaging, R. Guzzardi, Ed., Nijhoff, 1987;

(3) M. Garreau, J-L. Coatrieux, R. Collorec and C. Chardenon, "A Knowledge-Based Approach for 3-D Reconstruction and Labeling of Vascular Networks from Biplane Angiographic Projections," IEEE Medical Imaging, Vol. 10, No. 2, pp. 122–131, June 1991.

It is also possible to use a known process for the automatic geometric calibration of an X-ray imaging system like that described in French Patent Application No. 93 00804. Briefly, for an automatic calibration of this type, a phantom is used in which the balls are distributed step by step in a succession such that the altitudes of the balls, measured along the axis of rotation of the imaging system, and especially along an axis of the phantom, are monotonic, increasing (or decreasing) with a sequence number of the balls in the succession.

The calibration of the imaging system makes it possible, in particular, to determine the estimated mean axis of rotation Ax of the imaging apparatus around the object as well as the position of the source 2 and the geometric characteristics of the optical axes of the various images acquired. The calibration also makes it possible to define a virtual volume VV (the intersection of the various projection cones) surround-ing the object 1 and broken down into elementary volume elements Vi or "voxels." This volume VV, and therefore each voxel Vi, is spatially located in a repository, hereinafter called the calibration repository, one of whose axes, in this case the Z axis, is the same as the estimated axis of rotation Ax. It must be noted that in this case, the projection planes PPi into which the acquired images IAi are projected are generally not parallel to the axis Z.

The calibration also makes it possible to define for each acquired image IAi a projection matrix Pi that makes it possible to determine, for each voxel Vi, the coordinates of its projection (pixel) into the corresponding acquired image IAi.

Figure 3:
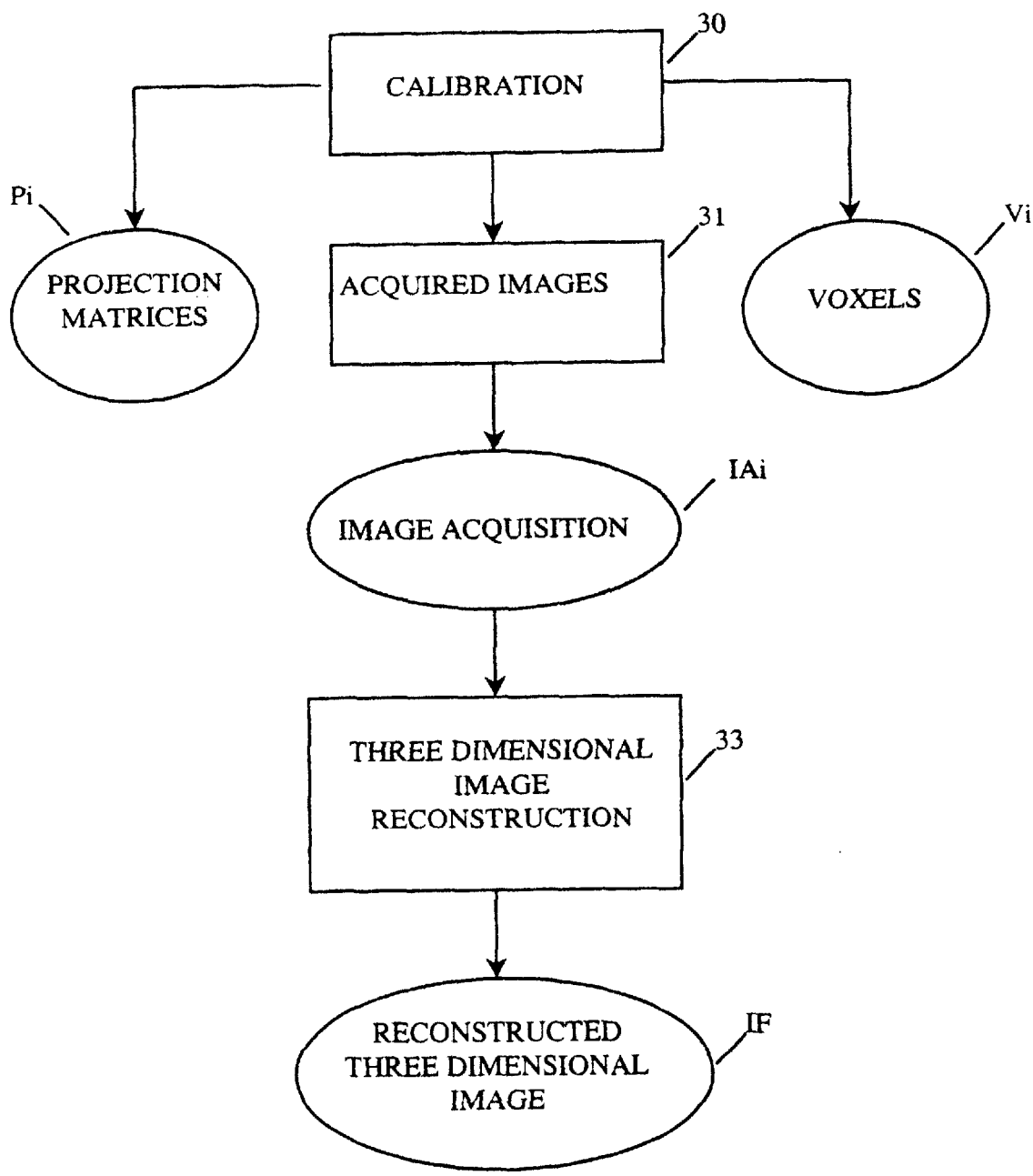
FIG. 3 is a flow chart of one mode of implementation of the process according to the invention.

A mode of implementation of the is described while referring more specifically to FIGS. 3 and 4.

The algebraic image reconstruction algorithm is applied directly to the acquired images IAi (obtained after the calibration 30 and the acquisition 31) in order to deliver the reconstructed three-dimensional image IF, typically with three iterations.

It must be remembered that the basic principle of the image reconstruction algorithm according to the invention consists of initializing the voxels of the volume to a predetermined initial value, for example the null value, and of subsequently performing a certain number of iterations, typically three. Each iteration comprises, for each acquired image, the projection of the voxels into the plane of each acquired image so as to obtain a virtual image, the determination of the difference between the projected volume (virtual image) and the corresponding acquired image, followed by the projection of this difference back into the volume.

Generally after three iterations, an estimated value representing the density of the contrast medium injected into the X-rayed vessels is obtained for each voxel, making it possible to display the three-dimensional cartography of these X-rayed vessels (the image IF).

As seen in FIG. 4, while the base resolution of the acquired images is typically equal to 512 (512×512 pixels), this base resolution is reduced to an initial resolution of one-half that (256), which amounts to regrouping the voxels of the volume into groups of eight, and to performing on each acquired image a regrouping of pixels into groups of four.

A first iteration (step 40) is then performed and first density values are obtained for each of the voxels of the volume VV1.

While the second iteration could theoretically be applied directly to this first volume VV1, it is particularly advantageous, in terms of reducing the calculation time, to have already eliminated some of the voxels from this first volume VV1.

More precisely, an elimination of voxels from the periphery of the volume VV1 is performed (step 41). In practice, this amounts to "peeling" the volume, i.e., removing a superficial layer from the surface of the volume having, for example, a "thickness" of three voxels.

An elimination of the isolated bright voxels is then performed (step 42). In other words, all the voxels having a density value higher than a predetermined threshold, and whose adjacent voxels do not have density values higher than this threshold, are eliminated.

Next, (step 43) an expansion of the bright voxels, i.e., an expansion of the voxels whose density value is higher than a predetermined threshold $t_3$, is performed. In practice, each voxel whose density value is higher than the threshold $t_3$ is assigned the maximum density obtained among the density value of said voxel and the density values of the voxels adjacent to this voxel.

At the end of this preprocessing phase, a remaining volume of voxels VV2 is obtained, on which two successive iterations of the image reconstruction algorithm will be performed.

Before performing the second iteration, those among the voxels of the volume VV2 whose density value is higher than a first predetermined threshold $t_1$ are selected. These voxels are then subdivided into 8 (step 44) so as to obtain subdivided voxels forming a first subset VV3 and corresponding to an image resolution of double the initial resolution, i.e., to the base resolution equal to 512. Those among the non-subdivided voxels of the volume VV2 that can be regrouped in accordance with a regrouping criterion (step 45) are selected. This set of voxels, regrouped into groups of eight, will be used to form a second subset of voxels corresponding to a resolution of half the initial resolution, i.e., to a resolution of 128.

The regrouping criterion is as follows:

A voxel can be regrouped with the seven adjacent voxels if the coordinates of its center are each a multiple of two and if the value of the density of each of the seven adjacent voxels is also less than the threshold $t_1$. If either of these two conditions is not met, then even if a voxel has a density lower than the threshold $t_1$, it cannot be re-grouped and will therefore remain as is. At the end of this first regrouping, a sub-set VV4 of regrouped voxels corresponding to a resolution of 128 is obtained, as well as a subset VV7 of non-regrouped voxels having a density lower than the first threshold $t_1$ and therefore corresponding to a resolution of 256.

Next, the same regrouping criterion is advantageously applied to the subset VV4, in order to perform a second regrouping of voxels that have already been regrouped so as to obtain a subset VV6 of voxels derived from the subset VV4 and again regrouped into groups of eight, and hence corresponding to a resolution of 64.

Since the same regrouping criterion is applied, a voxel of the subset VV4 could be regrouped with its seven adjacent voxels if the coordinates are multiples of two and if each of these seven adjacent voxels also has a density lower than the first threshold $t_1$.

The voxels of the subset VV4 that were not able to be regrouped a second time form the subset VV5, corresponding to the resolution 128.

Next (step 47), for each acquired image, a virtual image is generated which corresponding to the projection of the voxels into the acquisition plane of said acquired image.

This having been said, given the fact that the volume based on which this projection is performed is a multi-resolution volume, successive projections will be performed from successive subsets of voxels so as to define elementary virtual images which will be enlarged, then combined with the elementary projections corresponding to the subsequent subsets of voxels.

More precisely, from the subset VV6 corresponding to the resolution 64, an elementary virtual image with a resolution of 64 is generated by projection. Each pixel is then divided in four in order to obtain four times as many pixels and to enlarge this elementary virtual image so as to bring it to a resolution of 128.

Next, the voxels of the volume VV5 (corresponding to the resolution 128) are projected into the same plane, in order to define the elementary virtual image having a resolution of 128, which is added pixel by pixel to the preceding enlarged virtual image, also having a resolution of 128.

Thus, a composite image having a resolution of 128 is obtained, in which each pixel is again divided in four in order to obtain four times as many pixels, and in order to thereby obtain an enlarged virtual image having a resolution of 256.

The voxels of the subset VV7 are projected so as to obtain the elementary virtual image having a resolution of 256, which is combined with the enlarged image having a resolution of 256 in order to obtain the intermediate virtual image having a resolution of 256.

Finally, this intermediate image having a resolution of 256 is enlarged in a way similar to that just described, in order to obtain an enlarged image having a resolution of 512, which is added pixel by pixel to the projection of the voxels of the subset VV3, in order to ultimately obtain the virtual image IVi having a resolution of 512 and corresponding to the projection of the voxels of the volume VV2 in the plane of the acquired image IAi.

Then, the difference between the virtual image IVi and the acquired image IAi is calculated (step 48).

Lastly, a retroprojection of this difference (step 49) is performed in order to respectively correct the density values of the respective subsets VV3, VV5, VV6 and VV7.

Thus, corrected subsets VV30, VV50, VV60 and VV70 are obtained.

These successive projection, subtraction and retroprojection operations are performed for each of the acquired images IAi.

A third iteration is then performed and ultimately, a three-dimensional representation of the X-rayed object is obtained.

The image reconstruction algorithm according to the invention therefore operates, in the second and third iterations, on approximately 7 million voxels, which are split into about 6 million voxels having a resolution of 512, 300,000 voxels having a resolution of 256, 82,000 voxels having a resolution of 128, and 100,000 voxels having a resolution of 64.

This results in a reduction of the reconstruction time by a factor of 4.

Moreover, in practice, the first detection threshold $t_1$ is predetermined so as to have a maximum number on the order of 6 million, for the voxels having a resolution of 512.

These voxels having a resolution of 512 correspond to the X-rayed blood vessels, while the other voxels correspond to the adjacent and more distant areas.

In particular, the voxels having a resolution of 64 correspond, in the case of a brain X-ray, to the demi-hemisphere of the brain that is not involved in the injection of the contrast medium.

Various modifications in structure and/or function and/or steps may be made by one skilled in the art to the disclosed embodiments without departing from the invention.

What is claimed is:

1. A process for reconstructing a three-dimensional image of an object from a set of numbered projected two-dimensional images of the object obtained from various positions of an imaging around the object, comprising the steps of generating a calibrating a virtual volume surrounding the object and broken down into voxels acquiring the set of numbered projected two-dimensional images, and reconstructing the three-dimensional image from the projected acquired two-dimensional images and from an iterative algebraic image reconstruction algorithm, wherein a first iteration of the algorithm is performed with a predetermined initial image resolution so as to obtain, at the end of this first iteration, first density values for the voxels of the volume, at least one part of the voxels of the virtual volume is subdivided into several sets, respectively, corresponding to different image resolutions that are multiples or sub-multiples of the initial resolution, and during each subsequent iteration of the algorithm, the algorithm is successively applied to each of the sets of voxels.

2. The process according to claim 1, wherein during each sub-sequent iteration of the algorithm, a virtual image is determined for each projected acquired image, by successively combining the elementary virtual images respectively obtained from the projections of the corresponding sets of voxels into the acquisition plane of the projected acquired image.

3. The process according to claim 2, wherein the elementary virtual images are generated in the increasing order of the resolution values, beginning with the elementary virtual image corresponding to the lowest resolution value, and after an elementary virtual image is determined, a scaling is performed in order to obtain an enlarged virtual image whose resolution corresponds to that of the next elementary virtual image to be determined, and the enlarged virtual image is combined with the next elementary virtual image.

4. The process according to claim 3, wherein projected two-dimensional images having a predetermined base resolution are acquired, an initial resolution is chosen which is equal to a sub-multiple of the base resolution, and chosen from among the different image resolutions are the base resolution, the initial resolution, and at least one first additional resolution, which is a sub-multiple of the initial resolution.

5. The process according to claim 3, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

6. The process according to claim 5, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

7. The process according to claim 5, wherein the regrouped voxels which meet the regrouping criterion are regrouped in order to from a fourth set of voxels corresponding to a second additional resolution, which is a sub-multiple of the first additional resolution.

8. The process according to claim 2, wherein projected two-dimensional images having a predetermined base resolution are acquired, an initial resolution is chosen which is equal to a sub-multiple of the base resolution and chosen from among the different image resolutions are the base resolution, the initial resolution, and at least one first additional resolution, which is a sub-multiple of the initial resolution.

9. The process according to claim 2, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

10. The process according to claim 9, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

11. The process according to claim 9, wherein the regrouped voxels which meet the regrouping criterion are regrouped in order to from a fourth set of voxels corresponding to a second additional resolution, which is a sub-multiple of the first additional resolution.

12. The process according to claim 1, wherein projected two-dimensional images having a predetermined base resolution are required, an initial resolution is chosen which is equal to a sub-multiple of the base resolution, and chosen from among the different image resolutions are the base resolution, the initial resolution, and at least one first additional resolution, which is a sub-multiple of the initial resolution.

13. The process according to claim 12, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

14. The process according to claim 13, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

15. The process according to claim 13, wherein the regrouped voxels which meet the regrouping criterion are regrouped in order to from a fourth set of voxels corresponding to a second additional resolution, which is a sub-multiple of the first additional resolution.

16. The process according to claim 1, wherein a first density threshold is generated as a function of a predetermined selection criterion, each voxel having a density higher than or equal to the first threshold is subdivided into a first number of subdivided voxels, the first number being defined based on the relationship between the base resolution and the initial resolution, all of which subdivided voxels form a first set of voxels corresponding to the base resolution, at least some of the voxels whose density is lower than the first threshold and which meet a predetermined regrouping criterion are regrouped so as to form regrouped voxels which together form a second set of voxels corresponding to the first additional resolution, the number of regrouped voxels in each group being based on the relationship between the initial resolution and the first additional resolution, and in that the voxels whose density is lower than the first threshold and which do not meet the predetermined regrouping criterion form a third set of voxels corresponding to the initial resolution.

17. The process according to claim 16, wherein a voxel meets the regrouping criterion if each of the coordinates of the center of the voxel is a multiple of 2 and if the density of each voxel adjacent to said voxel is lower than the first threshold.

18. The process according to claim 16, wherein the regrouped voxels which meet the regrouping criterion are regrouped in order to from a fourth set of voxels corresponding to a second additional resolution, which is a sub-multiple of the first additional resolution.

19. The process according to claim 1, wherein the part of the voxels of the virtual volume that is subdivided is obtained by eliminating the voxels located in a layer of predetermined thickness of the surface of the volume.

20. The process according to claim 1, wherein the part of the voxels of the virtual volume that is subdivided is obtained by eliminating the isolated voxels whose density is higher than a second pre-determined threshold.

21. Process according to claim 1, wherein after the first iteration of the algorithm, each voxel whose density value is higher than a third predetermined threshold is assigned a density value equal to the maximum density value obtained among the density values of said voxel and the adjacent voxels.

* * * * *